(12) United States Patent
Zangooie et al.

(10) Patent No.: US 7,542,136 B2
(45) Date of Patent: Jun. 2, 2009

(54) FLIPPING STAGE ARRANGEMENT FOR REDUCED WAFER CONTAMINATION CROSS SECTION AND IMPROVED MEASUREMENT ACCURACY AND THROUGHPUT

(75) Inventors: Shahin Zangooie, Hopewell Junction, NY (US); Lin Zhou, LaGrangeville, NY (US); Roger M. Young, Warwick, NY (US); Clemente Bottini, Marlboro, NY (US); Robert J. Foster, Stormville, NY (US); Ronald D. Fiege, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 148 days.

(21) Appl. No.: 11/772,838

(22) Filed: Jul. 3, 2007

(65) Prior Publication Data

US 2009/0009763 A1    Jan. 8, 2009

(51) Int. Cl.
*G01N 21/01* (2006.01)
*G01J 4/00* (2006.01)
(52) U.S. Cl. .................. 356/244; 356/237.4; 356/369; 356/614; 356/600

(58) Field of Classification Search ................. 356/244, 356/237.2–237.6, 364–369, 600, 614, 625
See application file for complete search history.

(56) References Cited

U.S. PATENT DOCUMENTS

| 6,031,614 | A | 2/2000 | Michaelis et al. |
| 6,084,666 | A * | 7/2000 | Kindwall et al. ............ 356/244 |
| 6,757,059 | B2 * | 6/2004 | Ebert et al. ................. 356/244 |
| 6,771,372 | B1 * | 8/2004 | Traber ........................ 356/399 |
| 6,791,680 | B1 * | 9/2004 | Rosengaus et al. ....... 356/237.2 |
| 6,820,508 | B2 | 11/2004 | Lee |
| 6,858,859 | B2 | 2/2005 | Kusunose |
| 6,885,019 | B2 | 4/2005 | Fanton et al. |
| 6,917,420 | B2 * | 7/2005 | Traber ..................... 356/237.4 |
| 6,952,258 | B2 * | 10/2005 | Ebert et al. ................. 356/244 |
| 2003/0147076 | A1 | 8/2003 | Bowman |
| 2006/0033914 | A1 | 2/2006 | Ebert et al. |

* cited by examiner

*Primary Examiner*—L. G Lauchman
(74) *Attorney, Agent, or Firm*—Cantor Colburn LLP; Rosa Yaghmour

(57) ABSTRACT

A sample stage for performing measurements using an optical metrology system includes at least one sample section for retention of a sample, and components for controlling orientation of the sample section with relation to the optical metrology system. A method and a computer program product are provided.

3 Claims, 7 Drawing Sheets

Flipping Stage - 100

Optical Metrology
System - 500

FLIPPING STAGE ARRANGEMENT FOR REDUCED WAFER CONTAMINATION CROSS SECTION AND IMPROVED MEASUREMENT ACCURACY AND THROUGHPUT

BACKGROUND OF THE INVENTION

1. Field of the Invention

The teachings herein relate to thin film metrology and, in particular, to a stage for improved measurements.

2. Description of the Related Art

The use of optical metrology in semiconductor manufacturing and development has grown significantly over the past several years. The technologies provide the capability to perform measurements which yield a wide variety of critical parameters, including thickness, critical dimension, trench depth, side wall angle, doping, etc. Measurement parameters such as these were previously available only through expensive and invasive techniques such as electron microscopy cross sectional imaging. Another technique, that of optical metrology, may also be used to determine various parameters of a semiconductor.

Figure 1:
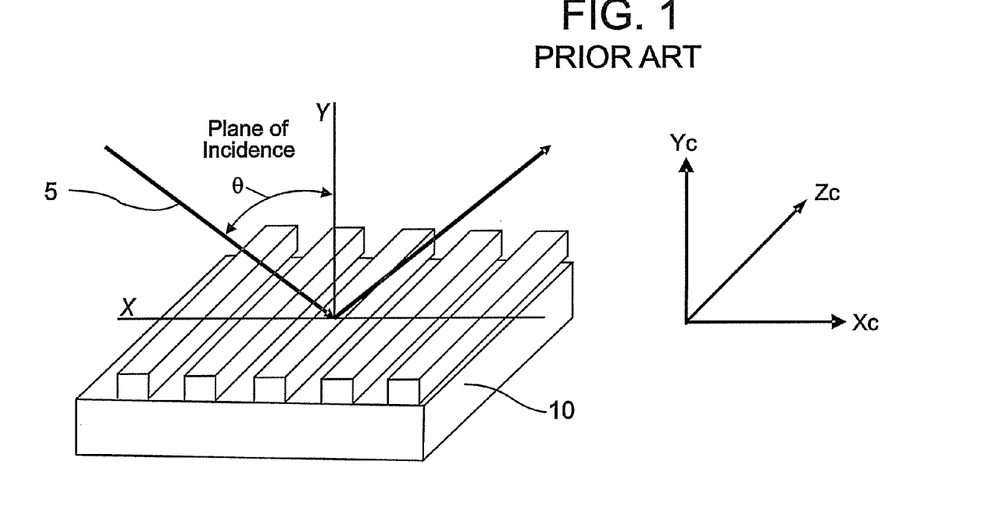
FIG. 1 depicts a prior art technique for optical metrology.
Figure 2:
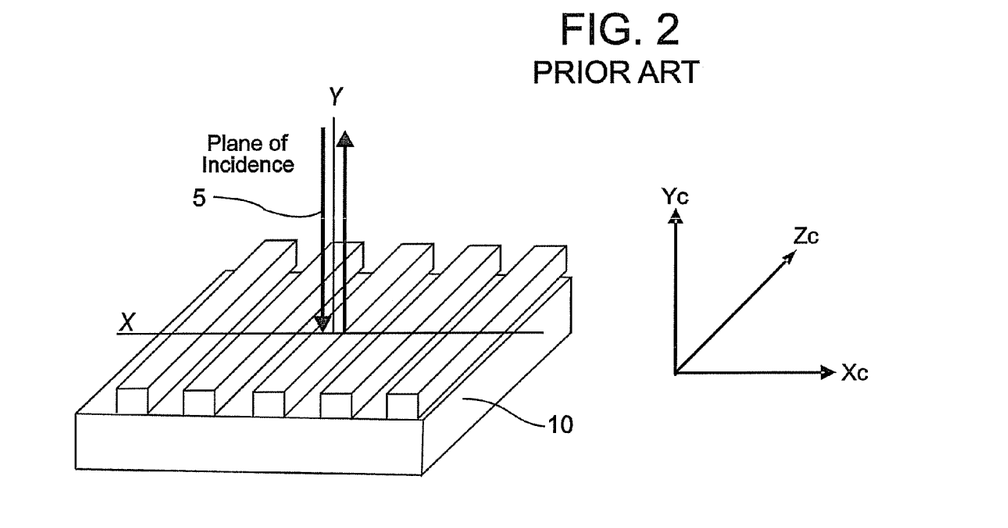
FIG. 2 depicts another prior art technique for optical metrology.

As a review, optical metrology generally may employ a variety of techniques. Common techniques include spectroscopic ellipsometry and reflectometry. Other types of optical metrology systems include those employing Raman spectroscopy, dark field and bright field wafer inspection, etc. In spectroscopic ellipsometry, and with reference to FIG. 1, an incident beam of measuring light 5 illuminates a target wafer 10 at an angle, $\theta$. The angle, $\theta$, is of a value that is other than normal to a surface of the wafer 10. Interrogation of the wafer 10 with measuring light 5 results in a spot (not shown). The spot resembles an ellipse. In reflectometry, and with reference to FIG. 2, the incident beam of measuring light 5 illuminates the target wafer 10 normal to the surface of the wafer 10. In most optical systems, reflectometry results in a circular spot.

The optical systems used in spectroscopic ellipsometry and reflectometry to illuminate the sample and collect the optical spectra generally make use of and control various wavelengths and other parameters to improve measurement results. Regardless of which type of optical system is used, reflected measuring light must be analyzed to determine properties of the target wafer 10. Analysis typically includes use of an optical model specifically created for the target being measured.

Advantageously, optical metrology provides information real-time using an in-linetool. A further benefit of optical metrology is that the technique does not involve contact with the sample (e.g., a semiconductor or a wafer). Unfortunately, several types of long-term measurements relying upon optical metrology can expose samples to environmental effects (such as particle contamination) and result in poor measurement results. Quite often, the wafers are placed face up on the stage with no or little protection against contaminants. Desorber techniques can be used to remove some of the contaminants and temporarily reverse the contamination impacts. However, use of desorber techniques can endanger integrity of some materials (such as photo resist) and may have irreversible consequences for product wafers. Hence, tighter manufacturing controls require new methods to promote fast and non-invasive measurements under well controlled conditions.

What are needed are techniques for improved measurement accuracy and precision during optical metrology. Preferably, the techniques provide for reducing or blocking wafer contamination during the various measurement processes.

BRIEF SUMMARY OF THE INVENTION

Embodiments of the invention include a sample stage for performing measurements using an optical metrology system, the sample stage including: at least one sample section for retention of a sample, and components for controlling orientation of the sample section with relation to the optical metrology system.

Also disclosed is a method for performing measurements with an optical metrology system, including: loading the sample onto a stage; adjusting a position of the stage to reduce a contamination cross section of the sample; and performing the measurements.

In addition, a computer program product stored on machine readable media including instructions for performing measurements with an optical metrology system, is provided and includes instructions for: controlling orientation of a measurement stage by at least one of rotating and translating the stage.

Other systems, methods, and/or computer program products according to embodiments will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

The detailed description explains the preferred embodiments of the invention, together with advantages and features, by way of example with reference to the drawings.

DETAILED DESCRIPTION OF THE INVENTION

Disclosed herein is a flipping stage for providing a reduced contamination cross section of a wafer. Use of the flipping stage results in improved measurement accuracy as well as throughput.

Some general and non-limiting definitions are now supplied for convenience. The term "wafer" generally refers to semiconductor substrates and semiconductor circuits built onto such substrate. Accordingly, as used herein, the term "wafer" generally applies to samples of semiconductor substrates and fabrications. It is considered that wafers are generally formed of a plurality of layers, such as thin films, using techniques as are known in the art. Aspects of wafers may be at least one of sampled and evaluated during and after fabrication. Aspects include film thickness, quality, presence, dimension(s), depth, angle, doping and other such aspects as are known in the art. The term "flipping stage" makes reference to the sample stage disclosed herein as well as the various components that provide for the functionality described.

Referring back to FIGS. 1 and 2, it should be noted that the measuring light 5 is directed the target wafer 10 with reference to a coordinate system in which the target wafer 10 exists. More specifically, a plane of incidence exists in an X-direction and a Y-direction. In the prior art, this coordinate system typically agrees with a conventionally selected coordinate system (shown as having axes, $X_c$, $Y_c$, $Z_c$). That is, for example, the target wafer 10 often lies in a plane that is generally parallel to a convenient surface, such as that of a lab bench.

The flipping stage disclosed herein provides for retention of target wafers 10 during optical metrology processes. The flipping stage includes a variety of components and capabilities that provide for reduced contamination cross section as well as reduction of other environmental influences. Included with the flipping stage are various mechanical, electrical, processing and optical components (and combinations of these components). The flipping stage components provide for, among other things, control of orientation of the target wafer 10.

Figure 3A:
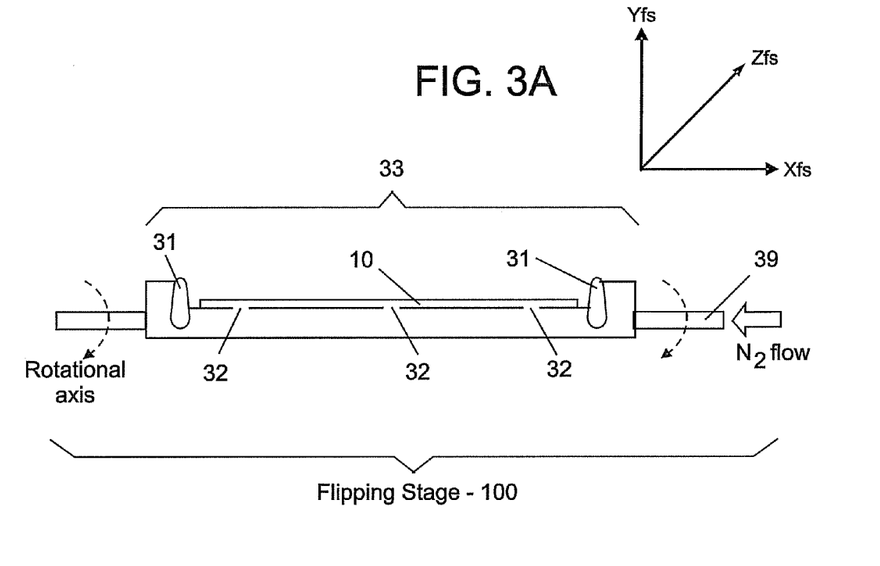
FIG. 3A and FIG. 3B, collectively referred to herein as FIG. 3, depict aspects of a flipping stage according to the teachings herein.

Referring to FIG. 3, aspects of the flipping stage 100 are shown. In FIG. 3A, the flipping stage 100 is shown in a home position (i.e., a conventional position). The home position may be used, among other things, for loading of the wafer 10. Included in the flipping stage 100 is at least one shower 31. In some embodiments, the shower 31 is a nitrogen ($N_2$) shower 31. Each shower 31 may include a shower head which is generally used for providing a curtain of gas (e.g., nitrogen) over the wafer 10. The gas is provided as a particulate free, or substantially particulate free, environment for addressing contamination problems by blocking particulates.

Figure 3B:
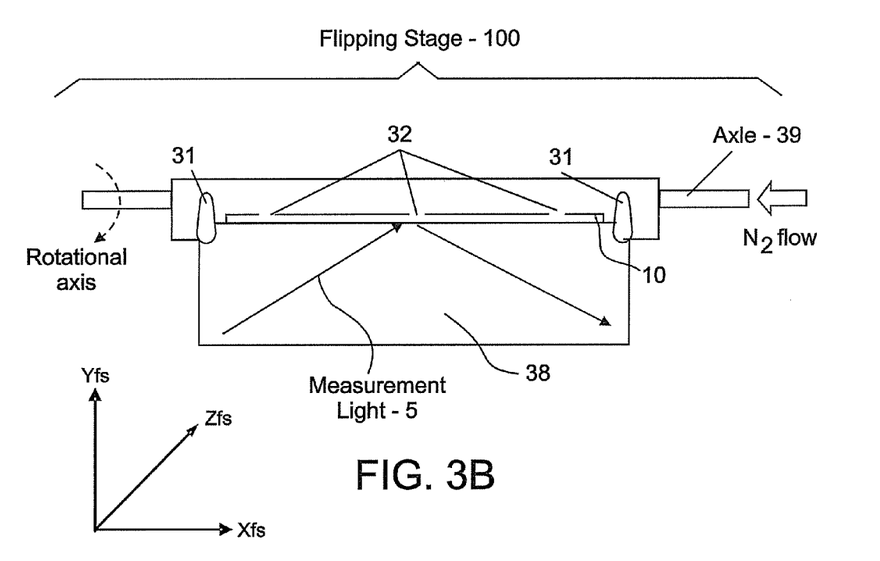

Retention of the wafer 10 is aided by at least one vacuum port 32. Each vacuum port 32 provides a desired retentive force upon the wafer 10. A sample section 33 which includes a retention area for retaining the wafer 10 is generally rotatable about a length (that is, the flipping stage 100 is adapted for lengthwise rotation). In this example, the flipping stage 100 is rotated about an X-axis, and may be considered to provide two-degrees of freedom (forward and reverse rotation about the X-axis). As shown in FIG. 3B, the nitrogen curtain 38 may involve all of the sample area 33 and some area beyond the sample area 33. This can be used beneficially for deflection of contaminant particles. In the example of FIG. 3, nitrogen gas is ported through an axle 39 for the carrying the sample section 33.

In some embodiments, the wafer 10 is first loaded face up (FIG. 3A). The wafer and flipping stage 100 is then rotated 180 degrees to a horizontal face down position. The nitrogen curtain 38 is then deployed to eliminate particles that did not leave the outer surface of the wafer during rotation. More specifically, the nitrogen curtain 38 can be used to create a positive pressure around the wafer 10 deflecting the remaining contaminants. A resulting nitrogen atmosphere has the added advantage that deep ultraviolet (DUV) measurements can be done in an environment involving less light absorption and better signal to noise ratio (SNR) than previously achievable.

Figure 4:
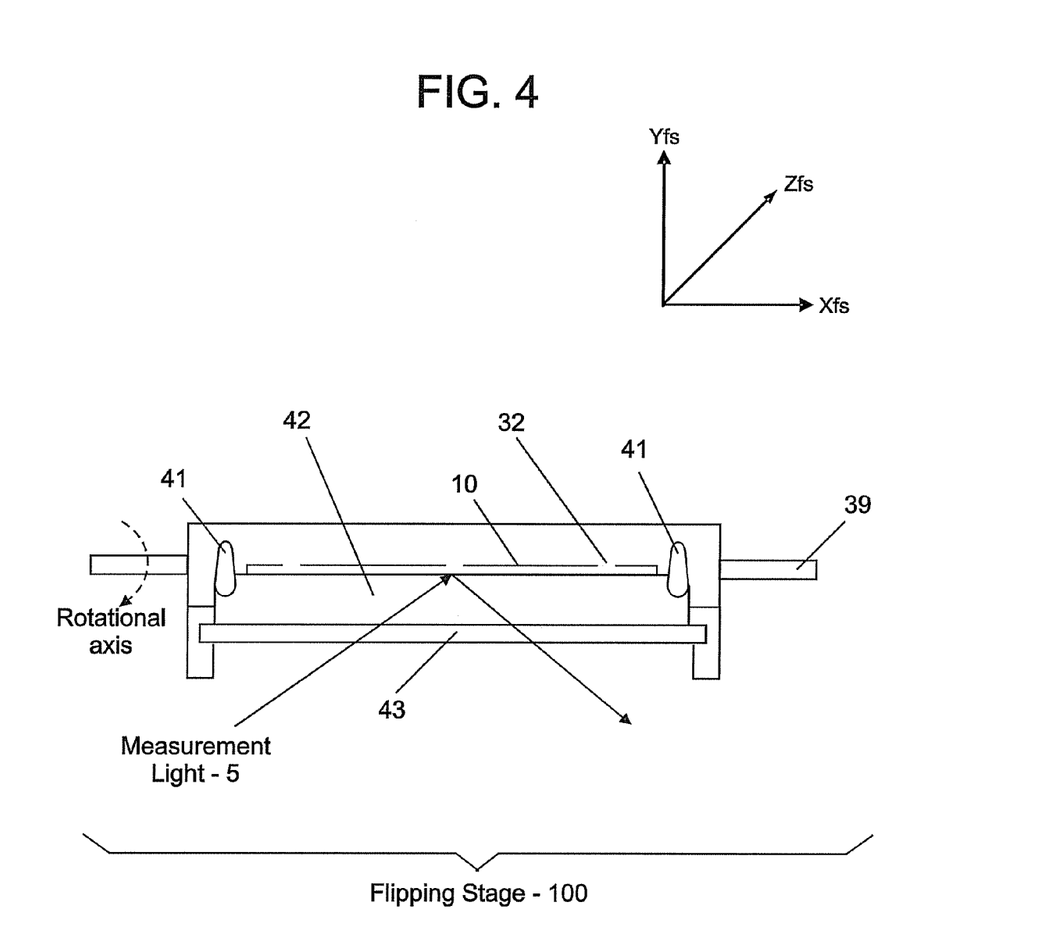
FIG. 4 depicts a closed environment for providing environmental control.

In addition to reduction of surface contamination problems, charged particle contamination effects can be reduced by grounding the wafer 10, thus leading away any static charge. A closed environment may further be created to provide for improved sampling controls. An exemplary closed environment, provided in FIG. 4, may include a vacuum or nitrogen (or other) atmosphere 42 and a measurement window 43, such as a transparent quartz glass or an equivalent.

Figure 5:
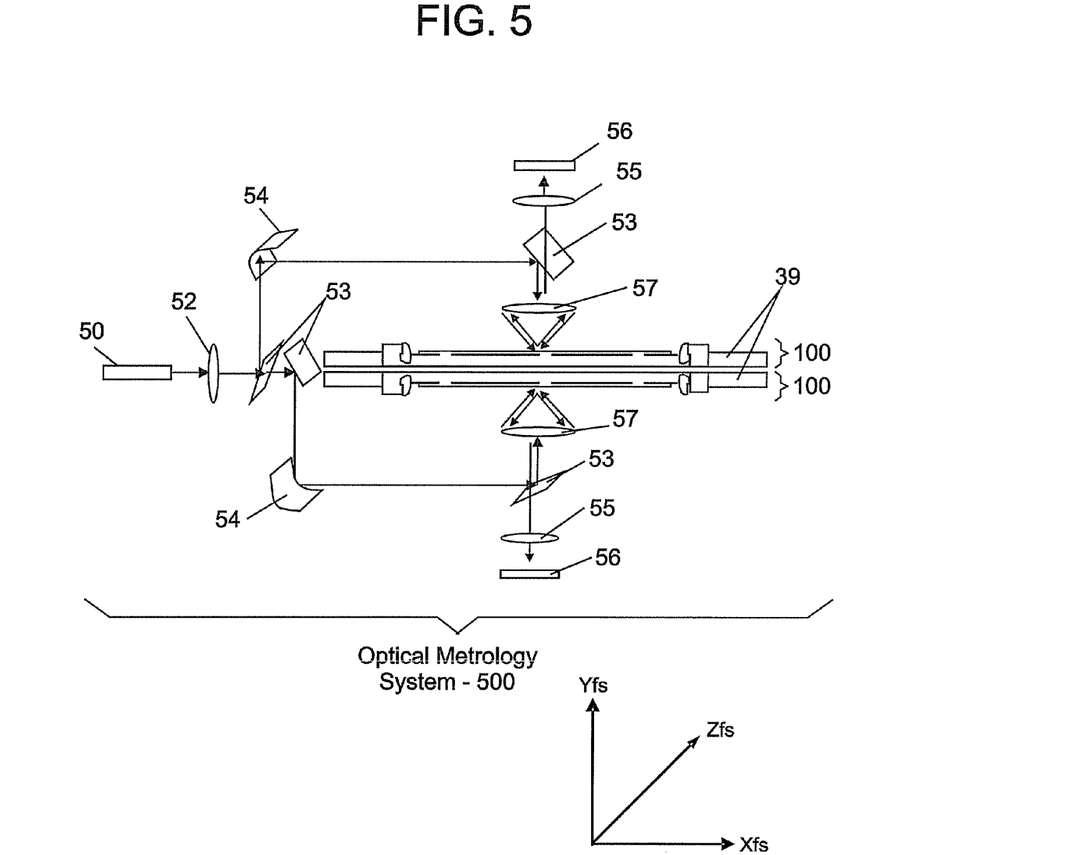
FIG. 5 depicts aspects of an optical metrology system for performing measurements in various orientations using multiple flipping stages.

Note that measurements may be done in either of the face up and face down positions. Reference may be had to FIG. 5.

In FIG. 5, aspects of an optical metrology system are shown in combination with the flipping stage 100. The system depicted provides for horizontal face up and face down measurements using a dual high numerical aperture (NA) lens angle resolved ellipsometer assembly, and may be referred to as a "polarized reflectometer system." A variety of other embodiments may be designed as will be recognized by one skilled in the art. Further, the design may provide for at least one of reflection and transmission measurement modes. The optical metrology system 500 depicted includes a light source 50, a polarizer 52, a plurality of beam splitters 53, mirrors 54, lenses 57, analyzers 55, detectors 56 and two flipping stages 100. In this embodiment, each sample section 33 is coupled to a separate axle 39. The separate axles may be moved together or independently, as dictated by needs of the user (and practical limitations). In this embodiment, the system 500 provides for performing measurement of characteristics of wafers 10 in the face up and face down positions using the two flipping stages 100. A similar embodiment to that of FIG. 5 is depicted in FIG. 6.

Figure 6:
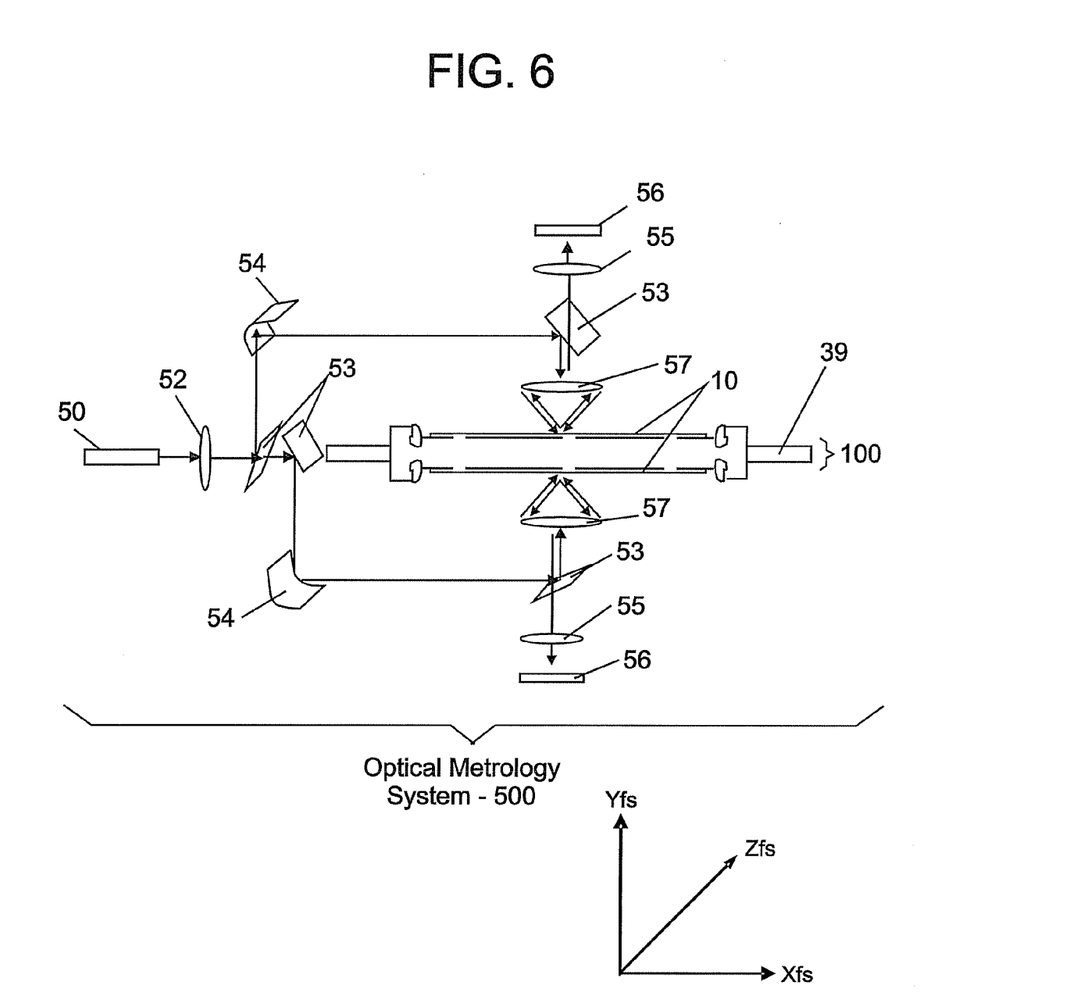
FIG. 6 depicts aspects of a double sided flipping stage with dual scanning optics.

In FIG. 6, a single, dual sided flipping stage 100 is depicted. The single, dual sided flipping stage 100 includes substantially the same elements as other embodiments of the flipping stage 100. However, in this embodiment, there is disposed upon a single axle 39 two sample sections 33. The two sample sections 33 are disposed 180 degrees apart. In other embodiments, additional sample sections may be included. For example, three sample sections 33 may be included with each one being about 120 degrees apart from the others. A further embodiment is depicted in FIG. 7.

Figure 7:
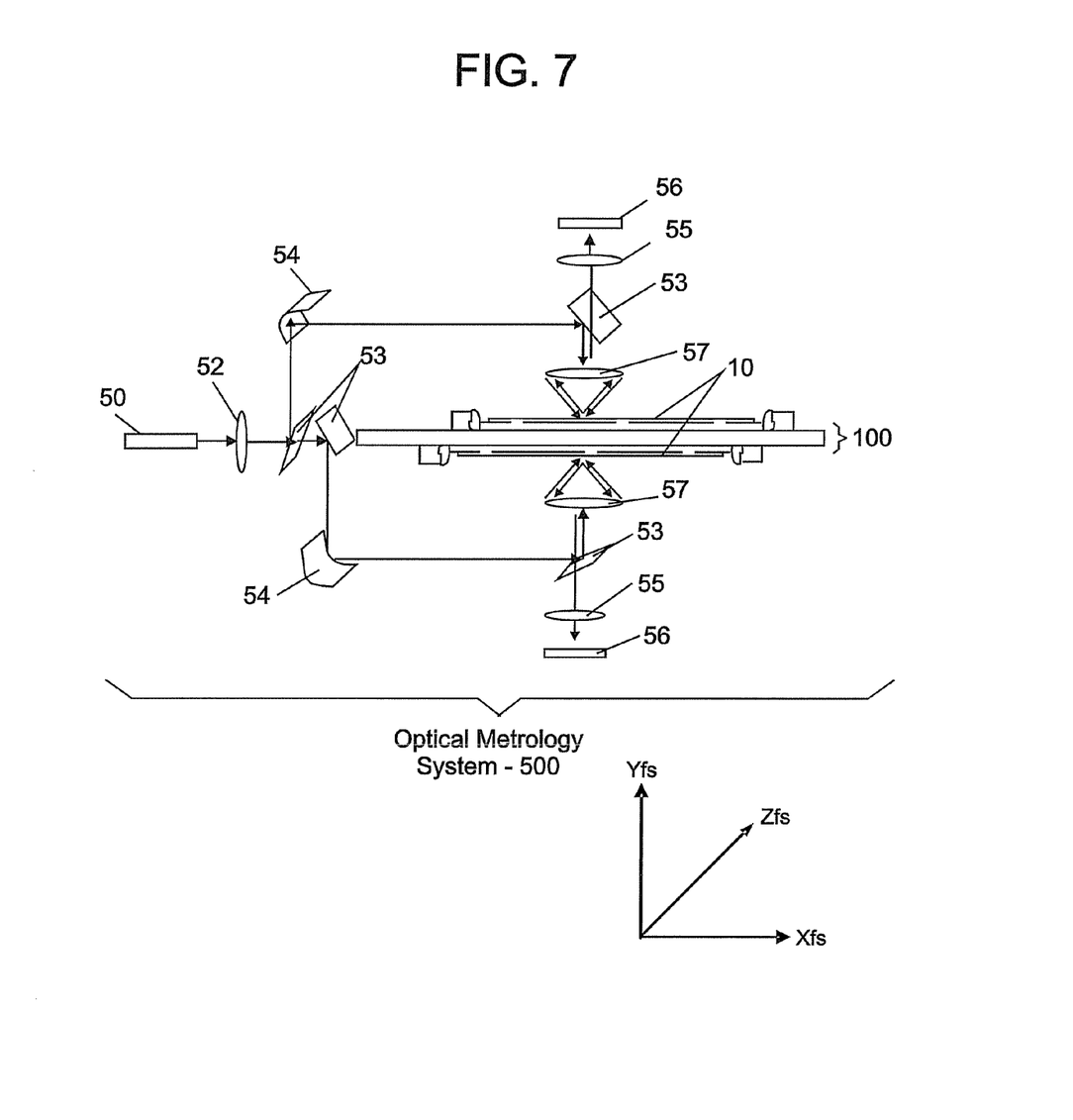
FIG. 7 depicts aspects of a double sided flipping stage with dual scanning optics, where at least one sample section is adapted for translational movement.

In FIG. 7, the flipping stage 100 is also equipped to provide for translational movement. That is, the sample section 33 may be adapted for moving along the X-axis. With reference to FIG. 7, the sample section 33 may move to the left or the right. In this regard, it may be considered that the flipping stage 100 may provide another two degrees of freedom (in this example, left and right translation). Of course, capability for translational movement may be combined with capability for rotational movement, as well as other forms of movement for controlling orientation of the wafer 10. A further embodiment is depicted in FIG. 8.

Figure 8:
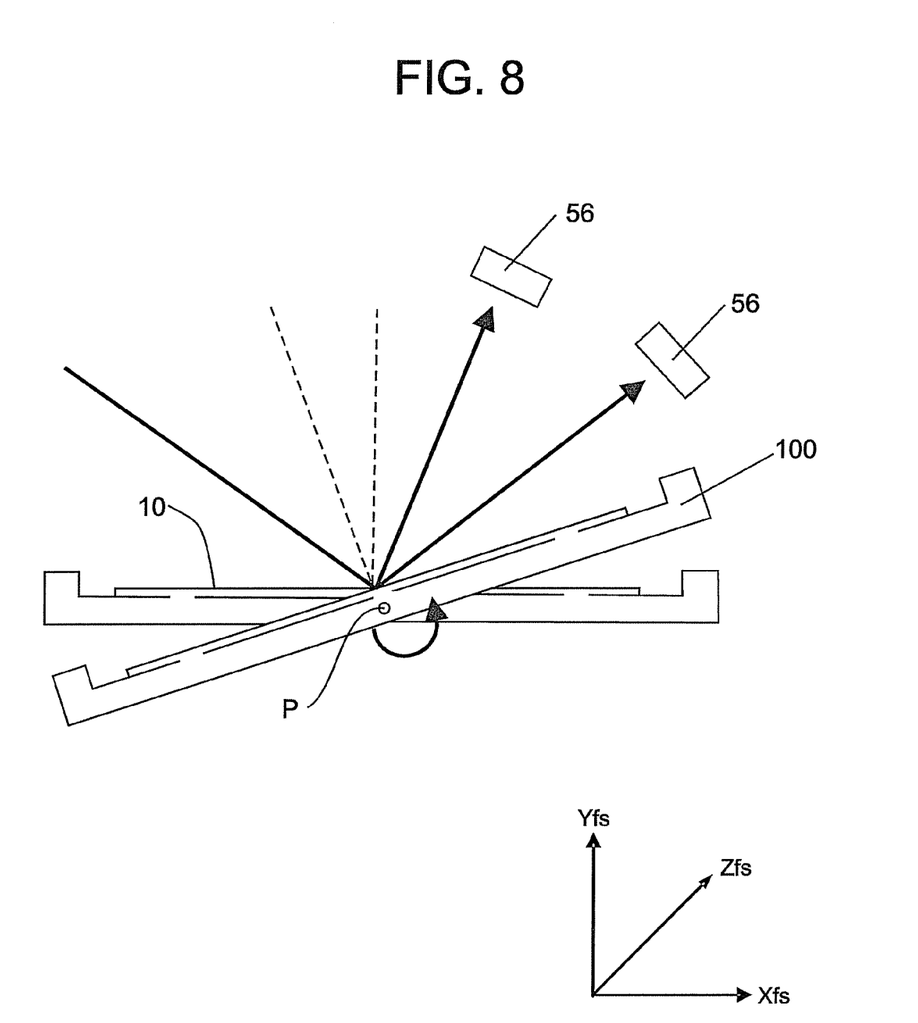
FIG. 8 depicts rotation of the flipping stage about a point.

In FIG. 8, multiple angle of incidence measurements (MAIM) are made possible. This is realized by adapting the flipping stage 100 for sidewise rotation about a point of rotation, P (up and down). Accordingly, the flipping stage 100 may be equipped to provide movement having another two degrees of freedom (wherein movement is about point P).

In general, optical metrology systems 500 may make use of a variety of embodiments of the flipping stage 100. That is, optics design may be provided to accommodate various embodiments, using, for example, appropriate mirrors shutters and beam splitters. The flipping stage 100 may improve measurement throughput using a double sided stage for simultaneous face up and face down horizontal measurements. Moving optics arrangements where optical heads scan wafers 10 independently may be had (refer to FIG. 6). A fixed optics arrangement and moving stage assembly where the stage can be considered as a two independent face down and face up components may be provided (FIG. 7). Further extension of a moving stage setup is in terms of multiple angle of incidence measurements (MAIM) capability shown in FIG. 8. MAIM increases the information richness and accuracy of many optical measurements. In the arrangements shown, it is possible to implement a wafer to wafer reference measurement resulting in improved measurement accuracy.

For example, using a flipping stage design with a single optics assembly and the reference chip mounted on the backside of the stage, the following measurement steps can be considered with no negative impacts on throughput. First, wafer loading and reference measurements may be completed. Subsequently, the flipping stage 100 is flipped. Afterwards, additional measurements are performed. Note that reference measurement may be performed during each wafer loading. Hence, impact on measurement throughput will be negligible.

One skilled in the art will recognize various techniques may be used in conjunction with the flipping stage 100. For example, reference samples may be used to provide for comparative measurements and analyses. The reference samples may be loaded in a stack with the sample 10, side-by-side or in some other arrangement. In addition, the flipping stage 100 may be used to provide for measurements of the sample 10 from either side. That is, an optically transparent sample section 33 may be used. Measurements may then be performed through the sample section 33. Accordingly, measurements of a frontside and a backside of the sample 10 may be completed.

As stated above, one skilled in the art will recognize that the flipping stage 100 may include a variety of components for enabling the flipping stage 100. Examples include, without limitation, computer controls, servos, relays, electric motors, measuring equipment, gears, supplies of at least one of a vacuum and an atmosphere, pressurized nitrogen, filtration or other purification systems, computer instructions stored on machine readable media for operating the flipping stage 100 in conjunction with the metrology system 500.

As described above, embodiments can be embodied in the form of computer-implemented processes and apparatuses for practicing those processes. In exemplary embodiments, the invention is embodied in computer program code executed by one or more network elements. Embodiments include computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Embodiments include computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A sample stage for performing measurements using an optical metrology system, the sample stage comprising:
    at least one sample section comprising at least one of a shower for blocking particulate deposition on the sample and a vacuum port for retention of a sample for retention of the sample, components for controlling orientation of the sample section with relation to the optical metrology system, wherein the components comprise components for providing at least one of lengthwise rotation, translational movement and sidewise rotation;
    and an apparatus for providing a closed environment for the sample, wherein the apparatus comprises at least one of a supply of vacuum, a supply of an atmosphere and a measurement window;
    wherein the sample stage is adapted for providing movement comprising between one and six degrees of freedom.

2. A method for performing measurements with an optical metrology system comprising at least a dual optical path and at least one of a movable optical element and a movable detector, comprising:
    loading the sample onto a stage;
    grounding the sample to remove static charge;
    activating one of a vacuum and a shower;
    adjusting a position of the stage to reduce a contamination cross section of the sample by at least one of rotating the stage from a face up position to a face down position, and moving the stage by at least one of lengthwise rotating the stage, sidewise rotating the stage and translating the stage; and
    performing the measurements by performing at least one of reflectometry measurements, spectroscopic ellipsometry measurements, transmission measurements;
    wherein performing the measurements comprises measuring from at least one of a backside and a frontside of the sample.

3. A computer program product stored on machine readable media comprising instructions for performing measurements with an optical metrology system, the product comprising instructions for:
    loading the sample onto a stage;
    grounding the sample to remove static charge;
    activating one of a vacuum and a shower;
    adjusting a position of the stage to reduce a contamination cross section of the sample by at least one of rotating the stage from a face up position to a face down position, and moving the stage by at least one of lengthwise rotating the stage, sidewise rotating the stage and translating the stage; and
    performing the measurements by performing at least one of reflectometry measurements, spectroscopic ellipsometry measurements, transmission measurements;
    wherein performing the measurements comprises measuring from at least one of a backside and a frontside of the sample.

* * * * *